United States Patent [19]

Swisher

[11] Patent Number: 5,743,894

[45] Date of Patent: Apr. 28, 1998

[54] SPIKE PORT WITH INTEGRATED TWO WAY VALVE ACCESS

[75] Inventor: David Rork Swisher, Maryland Heights, Mo.

[73] Assignee: Sherwood Medical Company, St. Louis, Mo.

[21] Appl. No.: 481,237

[22] Filed: Jun. 7, 1995

[51] Int. Cl.[6] .................................................. A61M 1/00
[52] U.S. Cl. ........................ 604/320; 604/4; 604/319
[58] Field of Search ................... 604/4–6, 319–321, 604/252, 408–410; 137/141, 872; 251/149–149.1

[56] References Cited

U.S. PATENT DOCUMENTS

| | | | |
|---|---|---|---|
| 3,515,127 | 6/1970 | Reymond | 128/2 |
| 3,707,972 | 1/1973 | Villari et al. | 128/349 R |
| 4,231,366 | 11/1980 | Schaef | 128/214 E |
| 4,744,785 | 5/1988 | Rosenthal et al. | 604/4 |
| 4,781,707 | 11/1988 | Boehringer et al. | 604/317 |
| 4,988,342 | 1/1991 | Herweck et al. | 604/321 |
| 5,041,087 | 8/1991 | Loo et al. | 604/83 |
| 5,055,198 | 10/1991 | Shettigar | 604/4 |
| 5,141,504 | 8/1992 | Herweck et al. | 604/317 |
| 5,184,652 | 2/1993 | Fan | 141/21 |
| 5,205,834 | 4/1993 | Moorehead et al. | 604/247 |
| 5,286,262 | 2/1994 | Herweck et al. | 604/321 |
| 5,380,314 | 1/1995 | Herweck et al. | 604/403 |

*Primary Examiner*—John G. Weiss
*Assistant Examiner*—David J. Cho
*Attorney, Agent, or Firm*—Ari M. Bai; Montgomery W. Smith

[57] ABSTRACT

A port and valve combination and related method of use for accessing the fluid flow within a medical fluid collection system. More specifically, the invention relates to the use of a spike port having a conventional two-way valve disposed therein for use in priming, sampling, aspirating and flushing fluids to and from a blood collection chamber of an autotransfusion system in the absence of a source of suction using a needleless syringe to access the system. The access port includes a Y-site connector having a distal port, proximal port and spike port. A two-way valve is partially disposed within the spike port with the proximal port being connected to and in fluid communication with the interior fluid pathway within the system. A distal opening serves as a receptacle for receiving the luer tip of a syringe in order to implement the related method. The preferred method of using the port/valve combination is to connect the luer tip of a syringe to the valve and use the syringe to prime, sample, aspirate, flush the fluid collection system or to inject medication into the circulatory system of the patient.

6 Claims, 10 Drawing Sheets

SPIKE PORT WITH INTEGRATED TWO WAY VALVE ACCESS

BACKGROUND OF THE INVENTION

1. Field of the Invention

This invention relates generally to an access port for use in accessing fluid collection devices. More specifically, the present invention relates to a valve disposed within the access port for accessing a medical fluid collection system. Even more specifically, the present invention relates to the use of a valve/access port combination for use in priming, sampling, aspirating and flushing fluids to and from a blood collection chamber of an autotransfusion system.

2. Prior Art

Blood recovered from a patient's body, called autologous blood, offers significant advantages over blood from donors, called homologous blood. Autologous blood from the patient reduces the risk of adverse reactions and transmission of infectious disease, has near normal oxygen carrying capacity and pH, conserves blood, and provides cost savings over the use of homologous blood. For these reasons, the practice of reinfusing autologous blood, known as autotransfusion, has become increasingly popular.

Autotransfusion may be used in a variety of situations to recover autologous blood from a patient. In an emergency room, autotransfusion is applied to patients suffering from chest trauma. In an operating room setting, it is used to recover shed blood lost during surgery.

Various autotransfusion systems have been developed. In U.S. Pat. No. 4,798,578 to Ranford, for example, there is disclosed a system for the sterile collection and filtration of blood or fluids from a patient into a chest drainage unit (CDU), and simultaneous reinfusing of such fluid back to the circulatory system of the patient using a separate heavy plastic transfer vessel to properly filter the blood. However, typical of conventional autotransfusion systems, the Ranford system requires an outside source of vacuum be applied in order to create the desired suction for moving the blood or fluid from the CDU's collection chamber to the filters of the transfer vessel for eventual reinfusion into the patient.

In situations where the practitioner wishes to prime the autotransfusion system in the absence of a readily available infusion pump, the practitioner must resort to priming the system through an access port sometimes available on some commercial infusion pump setups. This particular method of priming uses an access port interposed between the infusion pump and the patient to prime the system using a syringe and needle combination. To create a source of suction in this manner, the practitioner pulls back the plunger of the syringe when the needle is disposed within the access port until the syringe begins filling with fluid, thereby indicating that sufficient vacuum has been achieved.

Unfortunately, the drawback to the above technique is that not all commercial infusion pump setups have an access port or practitioner may lack a syringe and needle to prime the autotransfusion system in a situation where an infusion pump is not readily available. Further, such a technique is narrowly tailored for priming or sampling, but is ill-suited for other tasks such as flushing the system when clots become present in the collected blood.

As of yet, nothing in the prior art has addressed the problem of developing a multi-purpose access port that is interposed between a collection chamber of the CDU and the infusion pump that allows the practitioner to use only the luer of the syringe to access the port, so that a practitioner may prime, sample, or flush the system in the absence of a conventional vacuum source or needle-filled syringe.

Therefore, there exists a need in the medical device art for a multi-purpose spike port located outside the CDU, but interposed between the CDU and the autotransfusion pump, that easily couples the luer of a syringe with the opening of the spike port and provides a convenient means for priming, sampling, aspirating, flushing or injecting medication into the autotransfusion system.

SUMMARY OF THE INVENTION

In brief summary, the present invention relates to a multi-purpose access port and related method thereof for an autotransfusion system with a two-way valve that permits the practitioner to prime, sample, aspirate, flush or inject medication into the system where a commercial infusion pump is not available to facilitate the process. The access port comprises a conventional Y-site connector having a spike port, proximal port and an access port interposed between the CDU and the infusion pump of the system. A two way valve, having a receptacle for coupling with the luer tip of a syringe, is disposed within the access port and allows for fluid flow communication in the interior of the system for the purposes of priming, sampling etc.

The practitioner utilizes the access port by fitting the luer tip of the syringe into the two-way valve seated inside the access port. If priming is required, the practitioner simply pulls back the plunger of the syringe until blood or fluid from the collection chamber begins filling the syringe, thereby creating sufficient vacuum within the system. On the other hand, if sampling is needed immediately after priming the system, the practitioner merely continues withdrawing fluids until an ample amount appears in the syringe for a sample, or if no priming was required, then the practitioner just couples the luer of the syringe to the valve inside the access port and withdraws a sample.

Another preferred method of use for the access port is the practice of flushing the system when blood clots appear past the outlet of the collection chamber. To flush the system, the practitioner turns off the source of suction or infusion pump, couples the luer of the syringe filled with saline or other suitable fluid to the valve, and pushes the plunger forward, thereby forcing the solution into the interior of the system. This flushing action forces clotted blood back into the collection chamber and permits the practitioner a second opportunity to reinfuse the blood.

The practitioner may also inject medication into the system by again coupling the luer of the syringe to the valve of the access port and injecting the medication into the system where it can travel to the infusion pump and into the circulatory system of the patient.

Accordingly, a principle object of the present invention is to provide an access port for medical fluid collection devices.

Another principle object of the present invention to provide an access port for an autotransfusion system, interposed between the CDU and the infusion pump, for permitting direct access to blood or other fluids drained or shed by a patient.

A further object of the present invention is to provide a two-way valve, disposed within the access port, which includes a receptacle that permits the valve to directly couple with the luer tip of a syringe.

An additional object of the present invention is to provide a multi-purpose access port which allows the user to sample, aspirate, flush or inject medication into an autotransfusion system.

Another further object of the present invention is to provide an access port which allows the user to prime the autotransfusion system in the absence of an outside source of suction.

These and other objects of the present invention are realized in a presently preferred embodiment thereof, described by way of example and not necessarily by way of limitation, which provides for a multi-purpose access port which allows the user to directly access the inside of an autotransfusion system using a luer-tipped syringe and also permits the user to prime, sample, aspirate, flush and inject medication into the system in the absence of an infusion pump.

DETAILED DESCRIPTION

Figure 1:
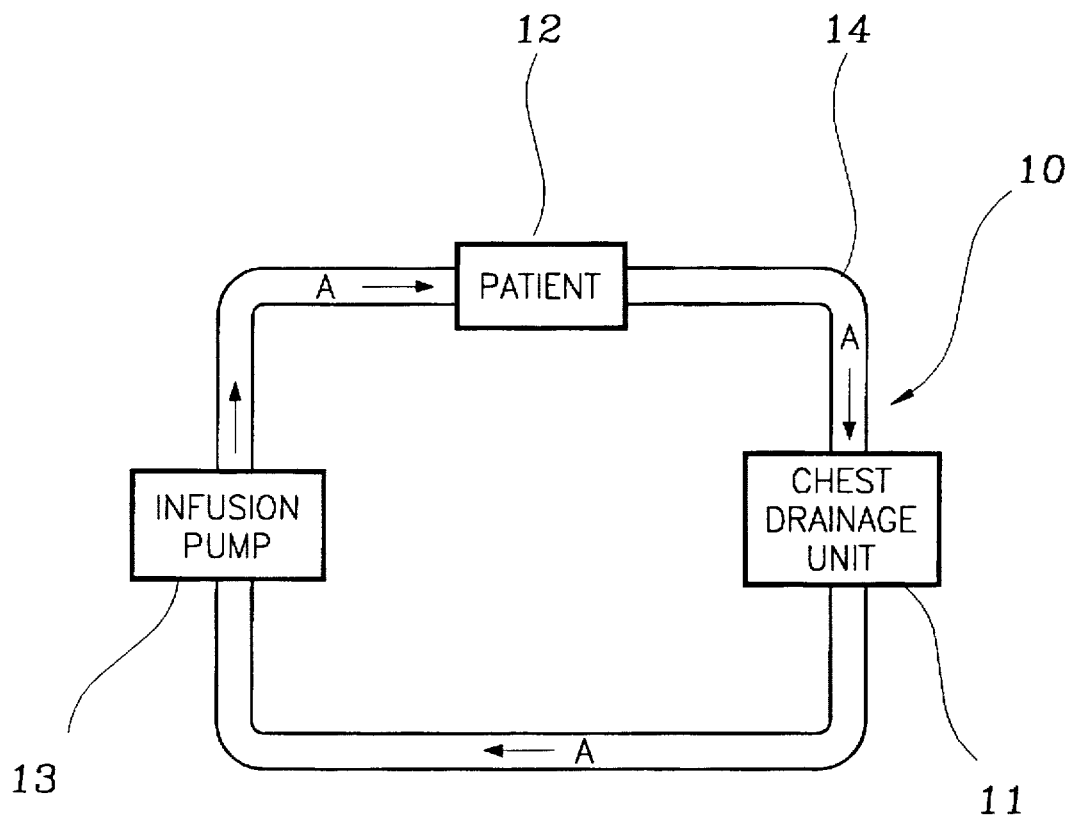
FIG. 1 is a simplified block diagram showing the basic operation of a prior art autotransfusion system.

A prior art autotransfusion system in accordance with the present invention is shown in FIG. 1. The basic configuration of an autotransfusion system 10 comprises a chest drainage unit (CDU) 11 for sterile collection and transfer of shed fluids from a patient 12, an infusion pump 13 connected to the CDU 11 for reinfusing the blood back to the patient 12, and flexible plastic tubing 14 for use as a conduit to transfer the blood between the autotransfusion system 10 and the patient 12. Fluid flow pathway A denotes the direction of the fluid flow within system 10.

The basic operation of an autotransfusion system is disclosed in U.S. Pat. No. 4,798,578 to Ranford and is herein incorporated by reference in its entirety. In short summary, the Ranford invention recites an autotransfusion system that operates using a CDU for the sterile collection of blood and fluids drawn from a patient, and simultaneous reinfusing of such fluids back to the circulatory system of the patient.

The general process of transfusing a patient's blood back to the patient begins by drawing fluids from the patient using a suction source located at the CDU which creates a positive air flow path through the system. The suction forces shed body fluids from the patient through plastic tubing and into the collection chamber of the CDU. As the fluid enters the collection chamber it is run through a gross filter which traps macroscopic debris such a blood clots, bone fragments and the like that become entrained in blood or other body fluids. Once the fluid is filtered, it is temporarily stored in the collection chamber where it is again filtered using a microemboli filter as the fluid exits the CDU. The fluid then runs through the plastic tubing and through an infusion pump where it is pumped back to the patient, thereby completing one complete autotransfusion cycle. Under prior art practice, priming and sampling would take place between the infusion pump and the patient using a commercial pump setup kit with a port to access the autotransfusion system.

Figure 2:
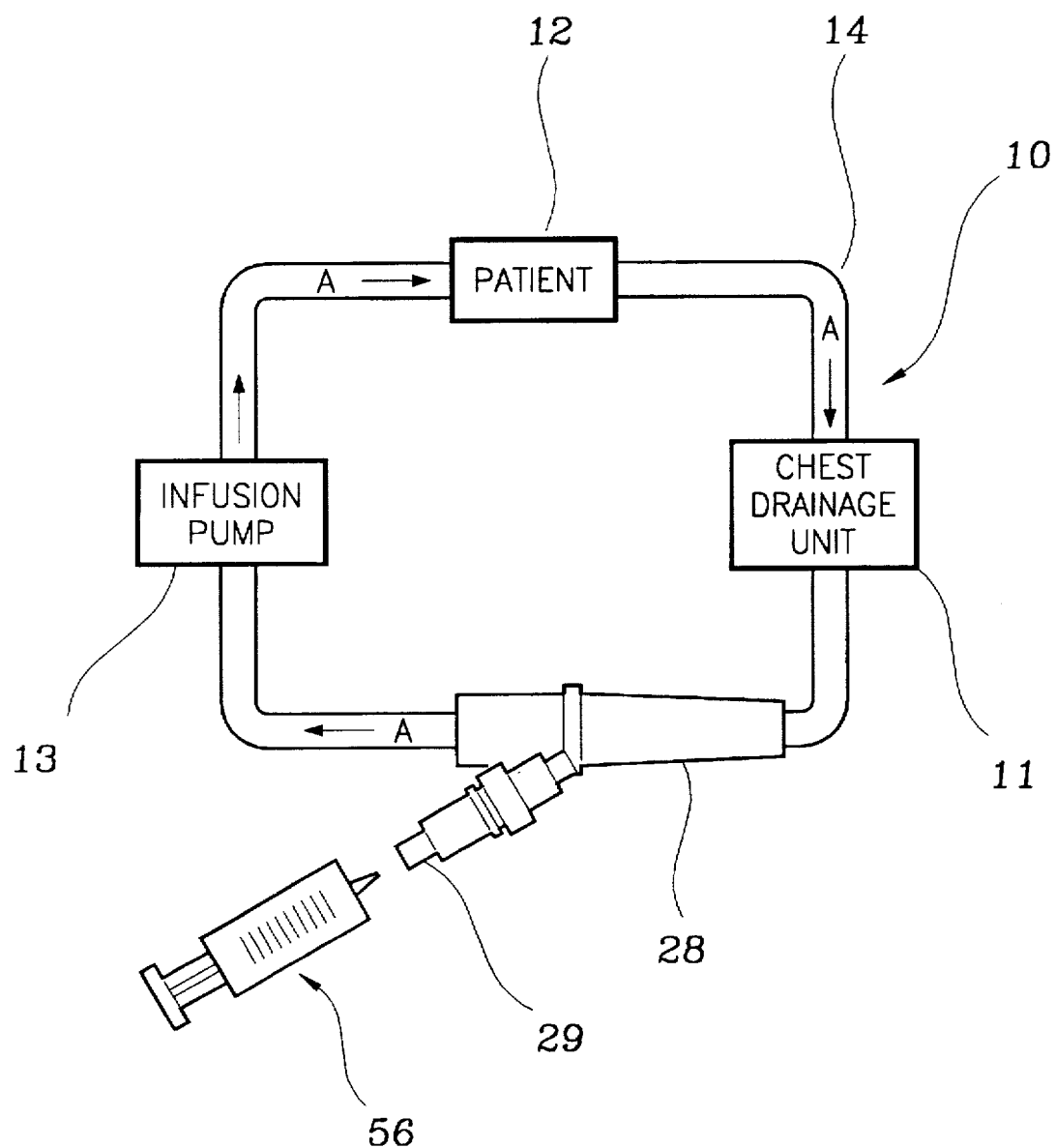
FIG. 2 is a cross-section of a prior art chest drainage unit showing its basic operative features, functions and air flow pathways.

Referring now to FIG. 2, the operative features of CDU 11 will be discussed in greater detail. The basic operation of an autotransfusion CDU 11 is disclosed in U.S. Pat. No. 4,988, 342 to Herweck et al and is herein incorporated by reference in its entirety.

In brief summary, an autotransfusion CDU 11 consists of a standard three chamber unit found in the prior art comprising a blood collection chamber 15, a water seal chamber 16 and suction control chamber 17. The purpose of the blood collection chamber 15 is to receive fluid drained from the patient's pleural and mediastinal space, but it may also function as a filtration site to filter blood and other fluids of unwanted debris. In an alternative embodiment, CDU 11 may be configured to have an additional second collection chamber separate from the CDU body which acts as the filtration site while the collection chamber 15 inside CDU 11 acts as an overflow chamber for the second detached chamber, as disclosed in the aforementioned Ranford invention.

The other two chambers, the water seal chamber 16 and suction control chamber 17 serve to control and regulate the air flow path A throughout CDU 11. The water seal chamber 16 prevents reflux of air and fluid back to the patient while the suction control chamber 17 regulates the degree of suction applied to autotransfusion system 10 and the patient. As shown in FIG. 2, the air flow pathway B is created by applying a source of suction (not shown) to an opening 18 located at the water seal chamber 16. The applied suction creates an air flow pathway B that forces fluid from the patient's body (not shown) through the tubing 19 and into the top of the collection chamber 15 where the air flow B passes through top portion of the collection chamber 15 and into the water seal chamber 16. Once in the water seal chamber 16, the air flow B travels down a first subchamber 20 and through a water seal 22 located at the bottom portion of the water seal chamber 16.

The water seal chamber 16 consists of a U-shaped chamber having a first subchamber 20 and a second subchamber 21 that form two vertical arms respectively with the water seal 22 located at the bottom portion where the two subchambers 20 and 21 meet. The water seal 22 functions as a protective one way valve allowing air to escape from the patient, while preventing contaminated atmospheric air from reentering the pleural cavity of the patient. By interposing a water seal 22 at the bottom portions of both subchambers 20 and 21, fluid is prevented from passing back through the water seal 22 due to the difference in pressure, thus preventing any kind of reflux action. The importance in preventing reflux is that under certain respiratory conditions, a sudden increase in pressure within the pleural cavity can appear, for example a cough or an air leak in the pleural cavity, which can produce a substantially higher pressure level within the pleural cavity itself and interferes with the normal respiratory function of the patient's lungs.

Once the air flow B passes through the water seal 22, it travels upward through the second subchamber 21 and is evacuated out of CDU 11 towards the suction source through tubing 23 that connects the CDU 11 and the suction source together. Further, the CDU 11 is designed so that air can escape through an automatic positive pressure relief valve (not shown) when an overpressure condition occurs inside the patient's pleural cavity. The bubbling action shown in the water seal 22 of FIG. 2 represents evacuated air from the first subchamber 20.

The suction control chamber 17 provides regulation of negative pressure (e.g. vacuum) during chest drainage. Vacuum within the CDU 11 is controlled by the height of water in the suction control chamber 17 which insures a continuous suction of the pleural cavity and also alleviates concerns over possible tissue invagination in the thoracic catheter during high levels of negative pressure within the cavity.

Figure 3:
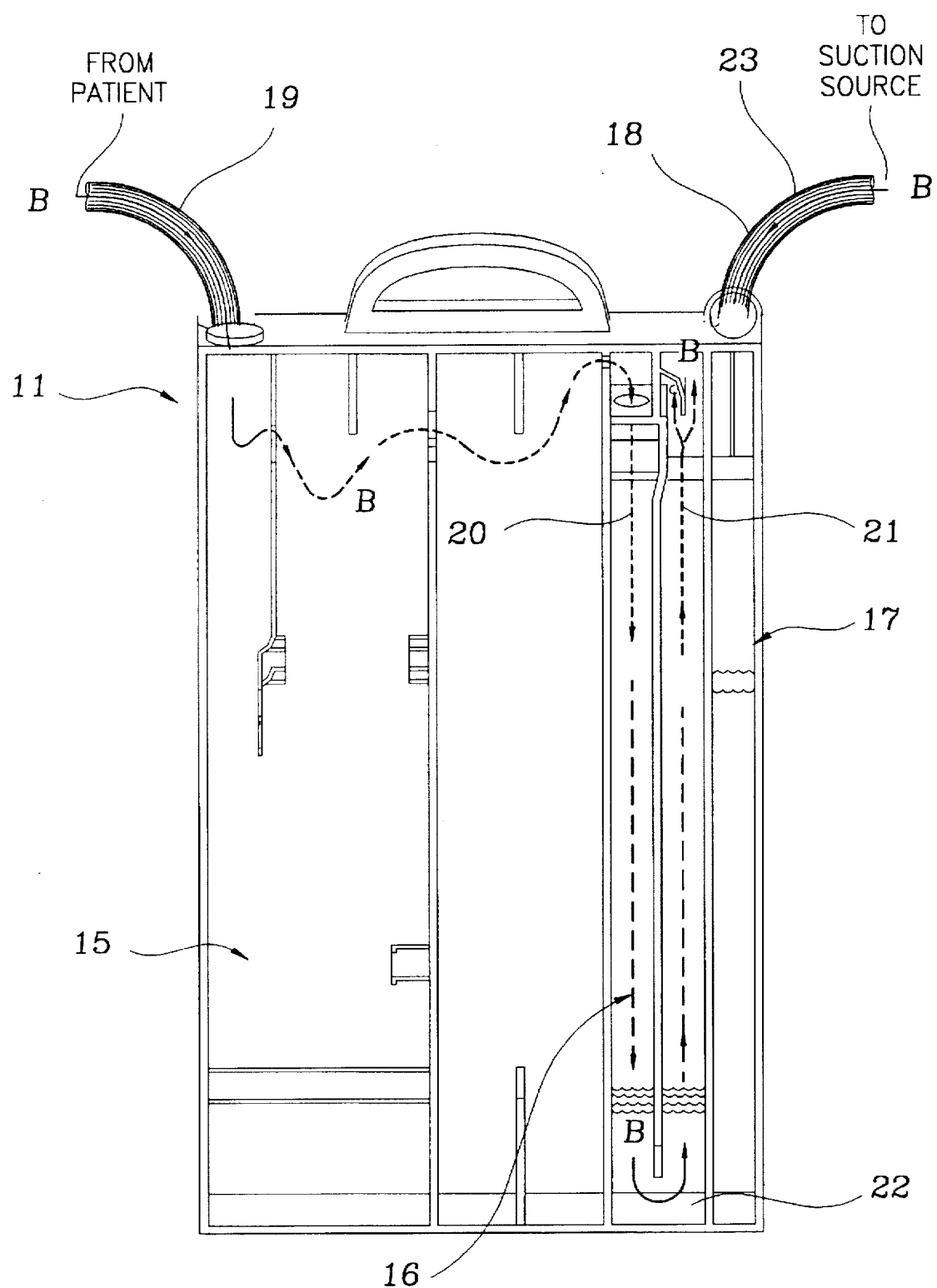
FIG. 3 is a cross section showing the a prior art embodiment of a suction control chamber preferred in use in the present invention.

In the configuration as shown in FIG. 3, the standard suction control chamber 17 can consist of a U-shaped chamber 24 having first and second subchambers 25 and 26 wherein a column of water 27 fills the bottom portion of chamber 17 and extends upward through both subchambers 25 and 26. First subchamber 25 is in fluid flow connection with both the water seal chamber 16 (not shown) and a suction source (also not shown) while a second subchamber 26 is open to atmospheric air which maintains an area of atmospheric pressure inside the first subchamber 25 above the water line. Air flow pathway C denotes the air flow throughout chamber 17. Pathway C shows atmospheric air being pulled into second subchamber 26 and into first subchamber 25 where it exits subchamber 25 to the suction source (not shown). At the same time, air flow is entering subchamber 25 from the water seal chamber 16 (not shown) and also exiting subchamber 25 for the suction source. The height of the column of water 27 interposed between the first subchamber 25 exposed to vacuum source pressure and the second subchamber 26 which is at atmospheric pressure determines the amount of negative pressure inside the collection chamber 15 and water seal chamber 16. For example, 20 cm of water at the column translates to a negative pressure of 20 cm inside the collection chamber. U.S. Pat. No. 4,439,190 to Protzmann et al gives a more detailed example of a typical suction control chamber of a CDU and its operation is herein incorporated by reference.

Figure 4:
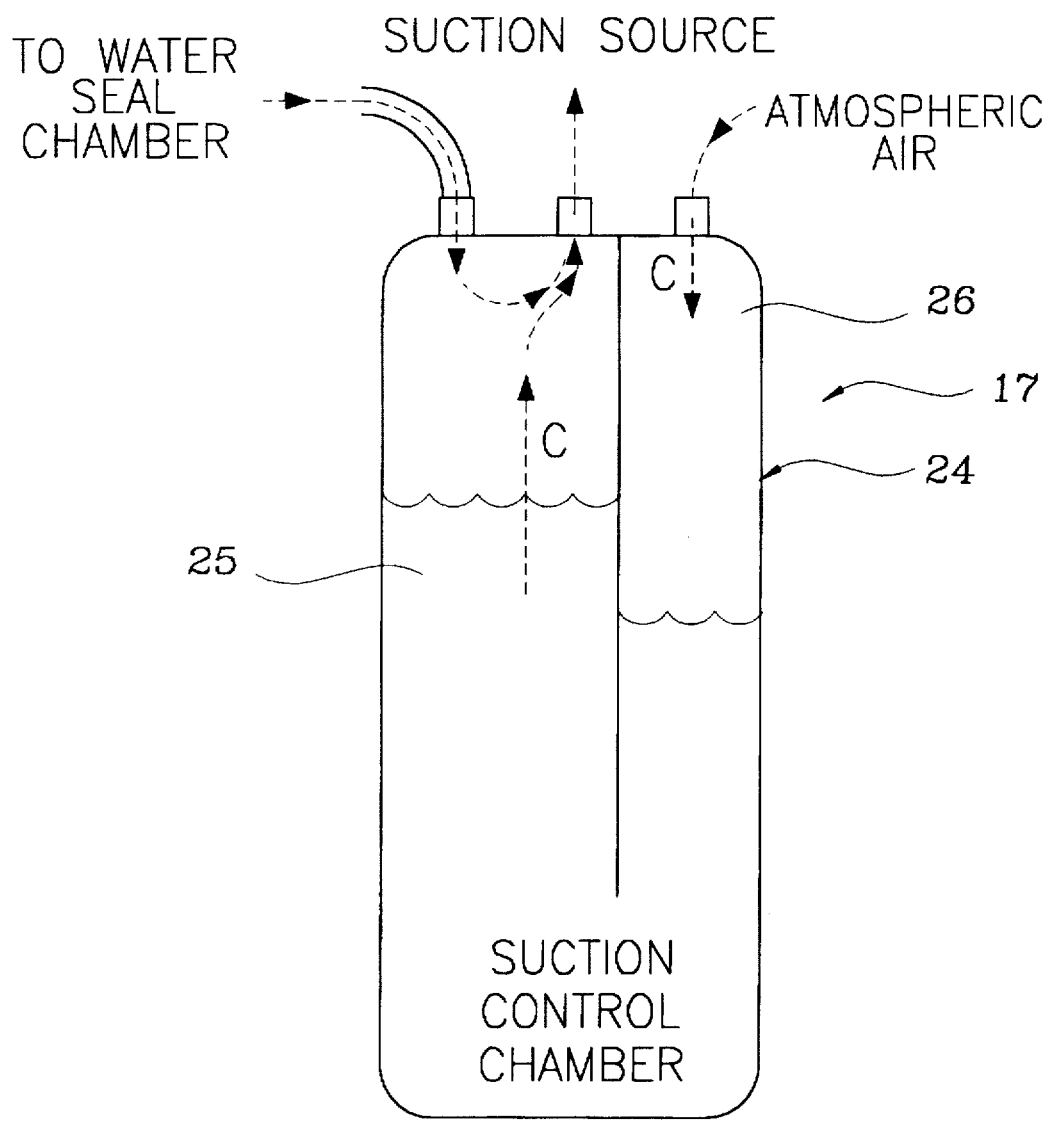
FIG. 4 is a simplified block diagram showing the basic operation of a prior art autotransfusion system as preferred in use with the present invention.

Referring now to FIG. 4, the configuration of the autotransfusion system according to the present invention will be briefly discussed. Instead of interposing the access port between the patient and the infusion pump, the present invention places a luer accessible access port between the CDU and the infusion pump so that a practitioner may access the autotransfusion system in the absence of an infusion pump or when the pump is not operable.

Figure 5:
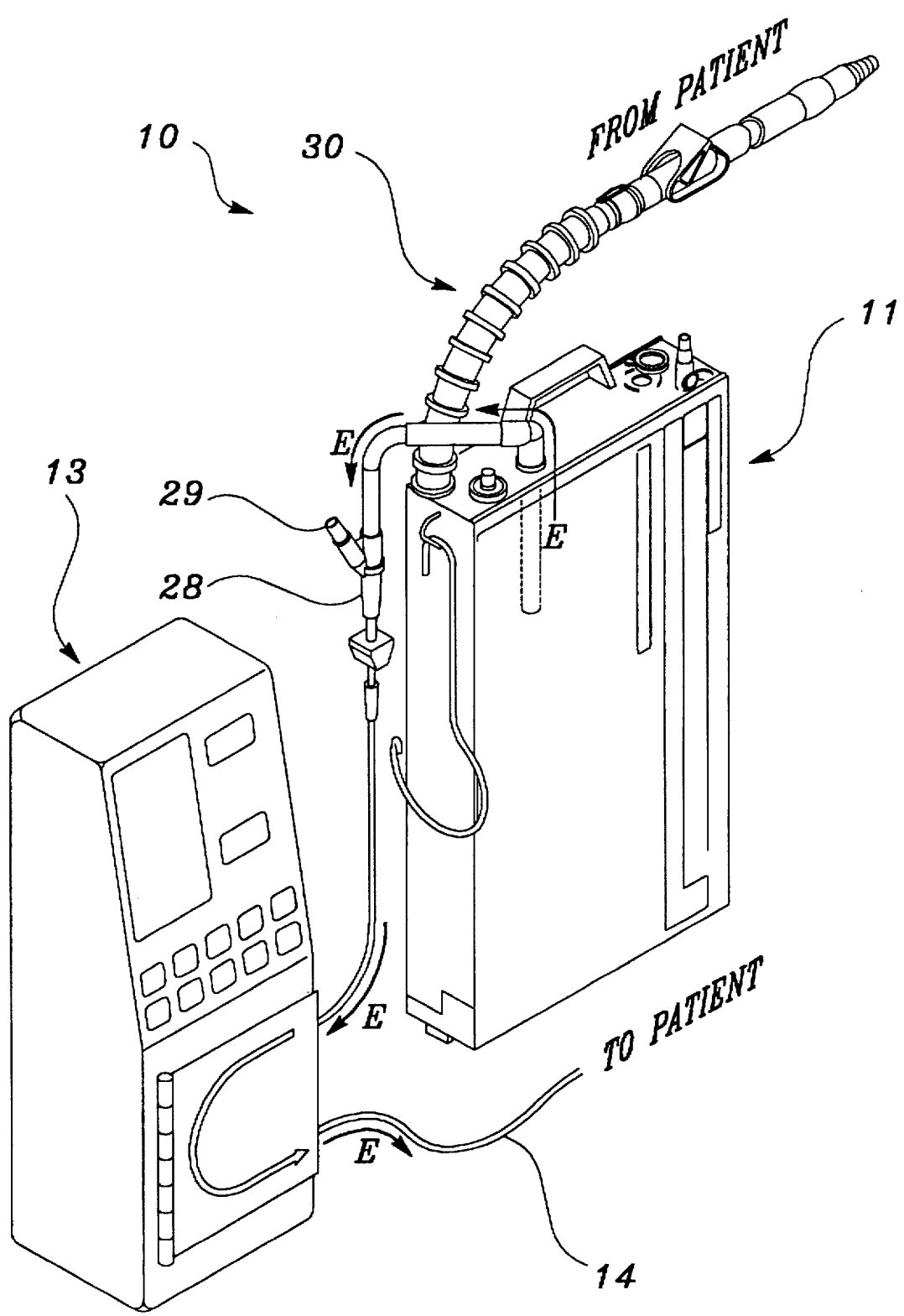
FIG. 5 is a perspective of an autotransfusion system showing the pump, Y-site connector with access port, and chest drainage unit in combination according to the present invention.

Referring now to FIG. 5, a perspective is shown of the autotransfusion system 10 of the present invention comprising a chest drainage unit (CDU) 11, infusion pump 13 and Y-site connector 28 with a two-way valve 29 disposed therein. In the preferred embodiment, the Y-site connector 28 is interposed between the CDU 11 and the infusion pump 13 and is connected to each by a flexible infusion tubing 14. Infusion tubing 14 may be made of any suitable flexible plastic, for example polyurethane or PVC, for use in transmitting fluids and gas throughout system 10. CDU 11 is connected to a patient (not shown) through a patient tube assembly 30 that attaches itself to collection chamber 15 of CDU 11.

The fluid flow pathway E of system 10 begins with the patient shedding blood or other body fluids which are drawn into a thoracic catheter (not shown) and travel through the patient tube assembly 30 and into the blood collection chamber 15. After filtration of the blood inside chamber 15, the blood travels out from the top portion of chamber 15 through infusion tubing 14 where it passes through the Y-site connector 28 and into a microaggregate filter 35. In alternative embodiments, the egress of blood from chamber 15 can be from any suitable site along the chamber 15 surface where the infusion tubing 14 may be attached. Once the blood passes through filter 35, it goes to infusion pump 13 where the blood is reinfused back to the patient.

Figure 6:
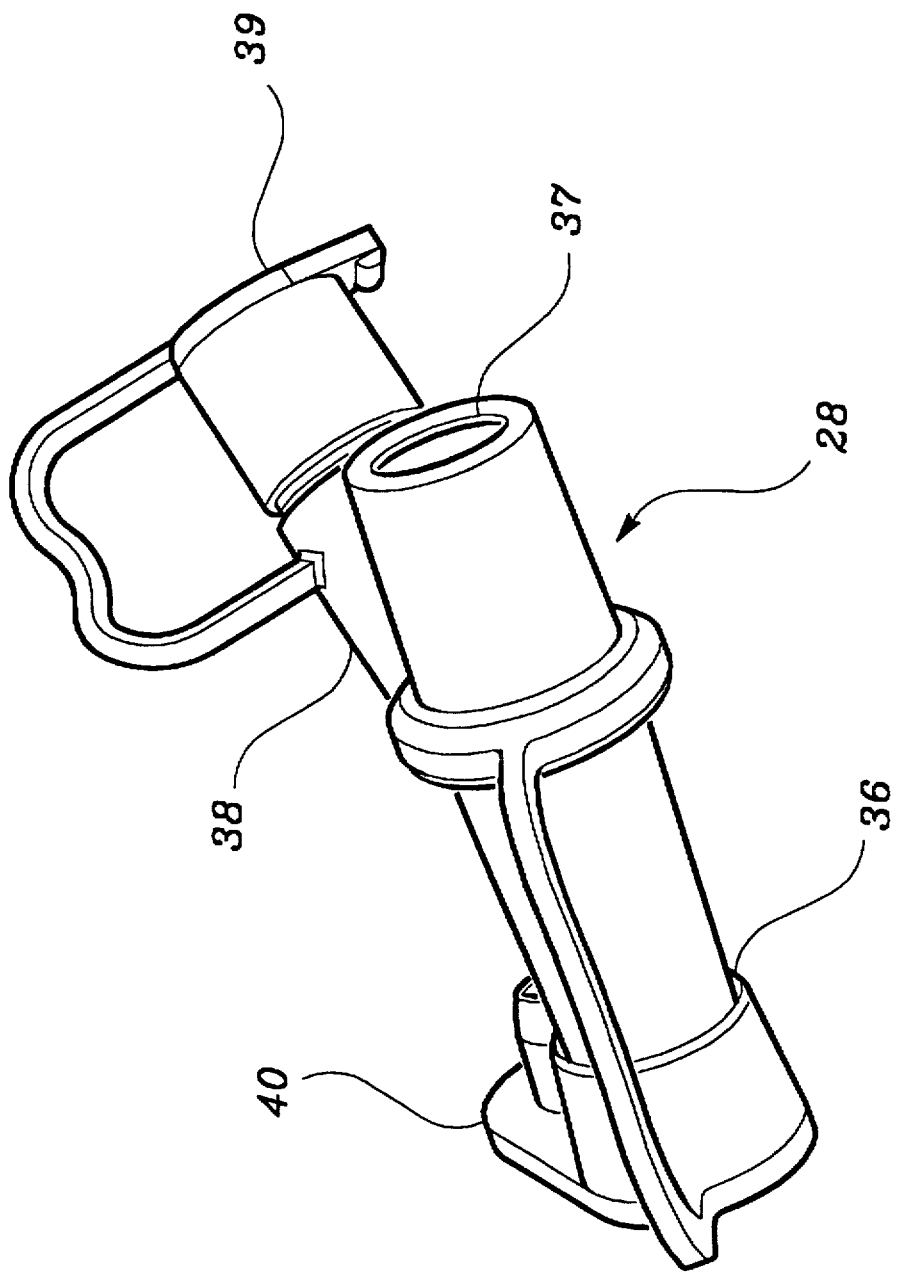
FIG. 6 is a perspective of the Y-site connector with optional dust cap and plug combinations also shown according to the present invention.

Referring now to FIG. 6, the Y-site connector 28 will be discussed in greater detail. Y-site connector 28 comprises a spike port 36 with a tethered first dust cap/plug combination port 40, a proximal port 37 bonded to infusion tubing 14 (not shown) leading from the collection chamber 15 and an access port 38 having a tethered second cap/plug combination 39 attached thereto. First and second cap/plug combinations 39 and 40 can either maintain a sterile closure about ports 36 and 38 when the dust cap element is used or seal both ports 36 and 38 from fluid flow communication therethrough by utilizing the plug element of combinations 39 and 40 instead.

Figure 7:
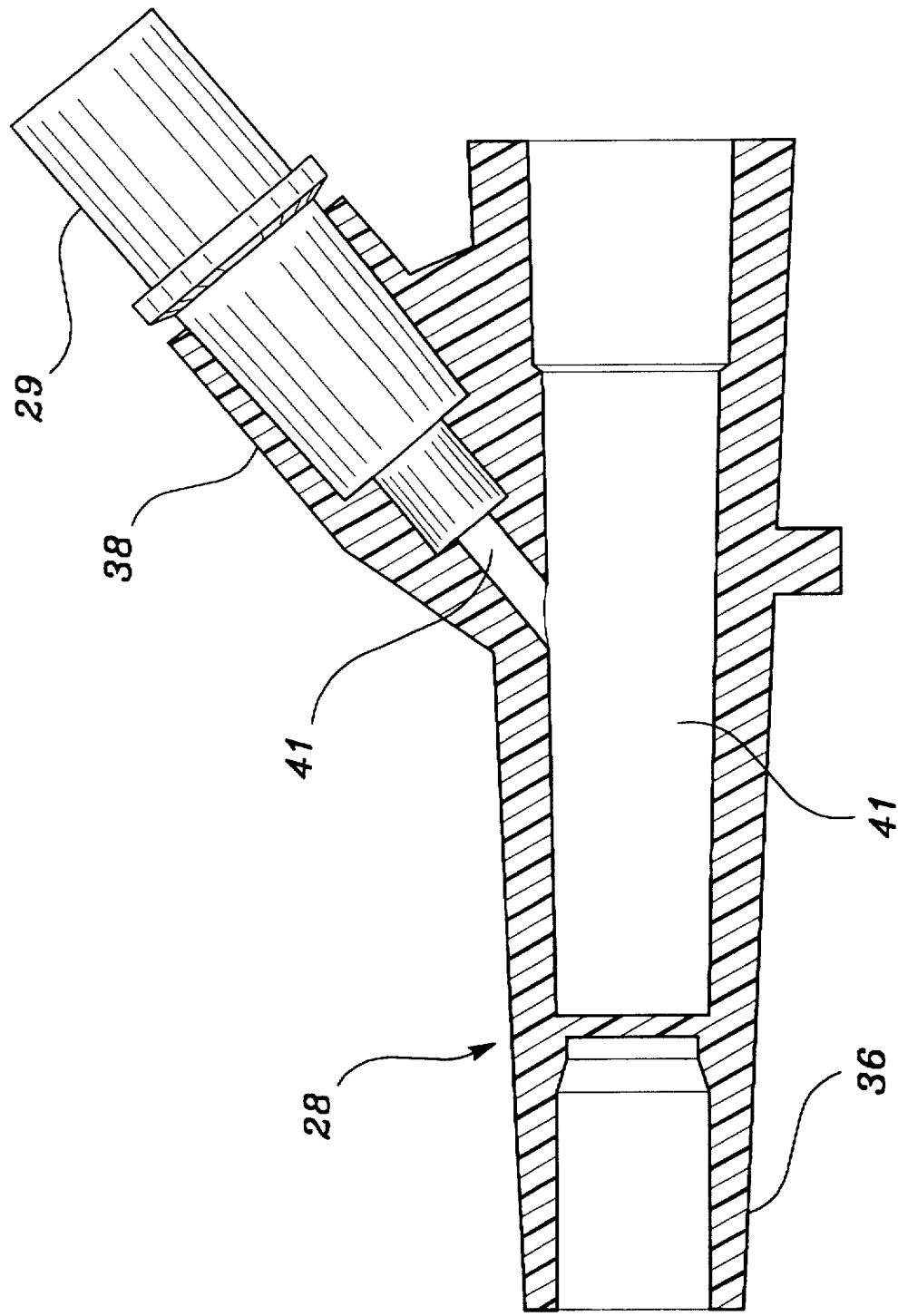
FIG. 7 is a cross-section of the Y-site connector according to the present invention.
Figure 8:
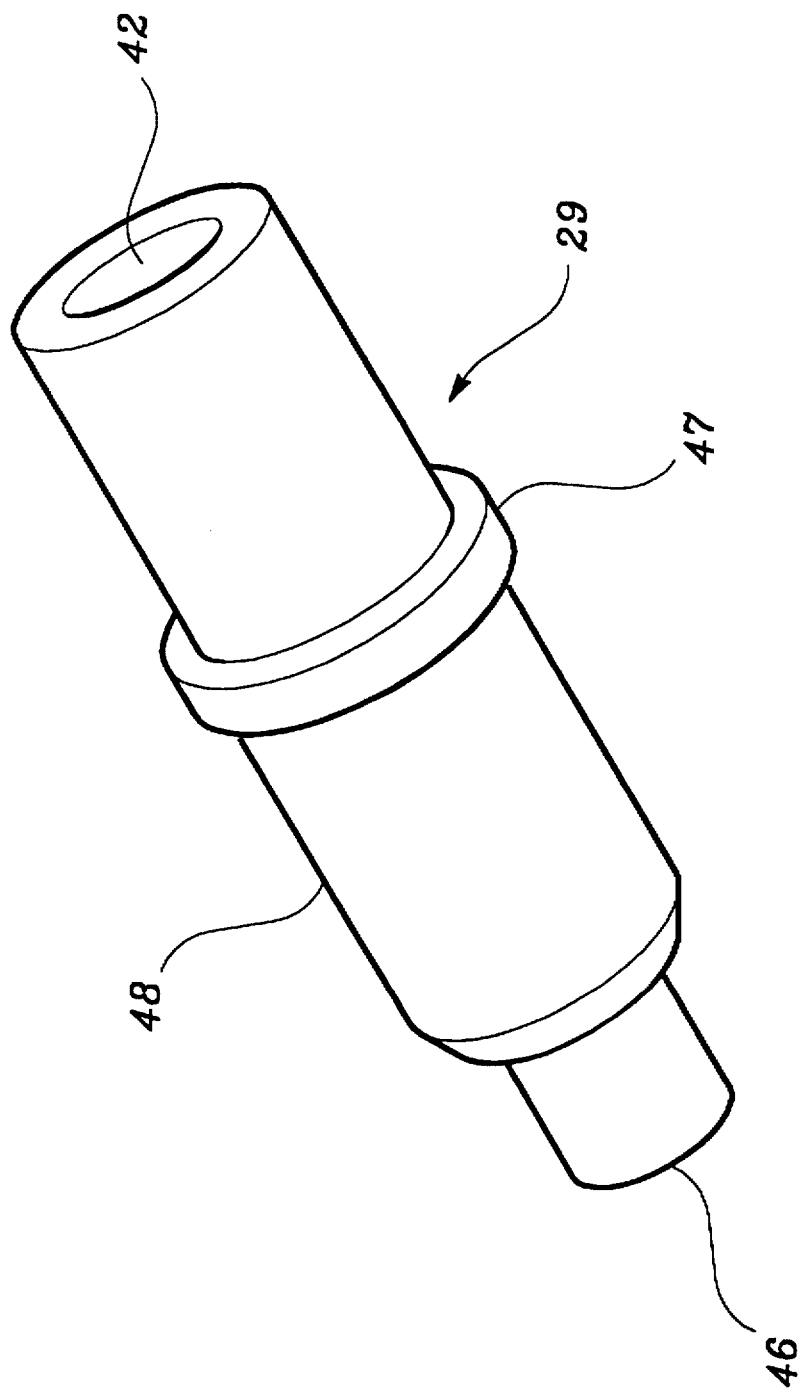
FIG. 8 is a perspective of the access valve according to the present invention.

Referring now to FIG. 7, a cross section of Y-site connector 28 is shown with access port 38 in fluid flow communication with the interior chamber 41 of connector 28. The access port 38 permits the practitioner access for the purpose of priming, sampling, aspirating or injecting medication into system 10. A two-way valve 29 is partially disposed within access port 38 for accessing interior chamber 41. The valve 29, shown in perspective in FIG. 8, is preferably a BESPAK valve manufactured by Bespak of Cary, N.C., which is a luer activated valve that is automatically closed to fluid flow communication whenever the luer tip of the syringe is removed from the distal opening of valve 29. Normally used as a valve for inflating the distal end of catheters inside patients in order to prevent removal of the catheter, the applicants are utilizing the BESPAK valve 29 for the novel purpose of permitting two-way access into an autotransfusion system 10.

As shown in FIG. 8, valve 29 has a tubular shape that comprises an annular distal opening 42, a proximal opening 46 and a flange 47. The flange 47 is positioned around the middle portion 48 of valve 29 and serves to hold the valve 29 in place inside the distal end of spike port 38 by having the flange 47 abut against the lip of the spike port 38.

Figure 9:
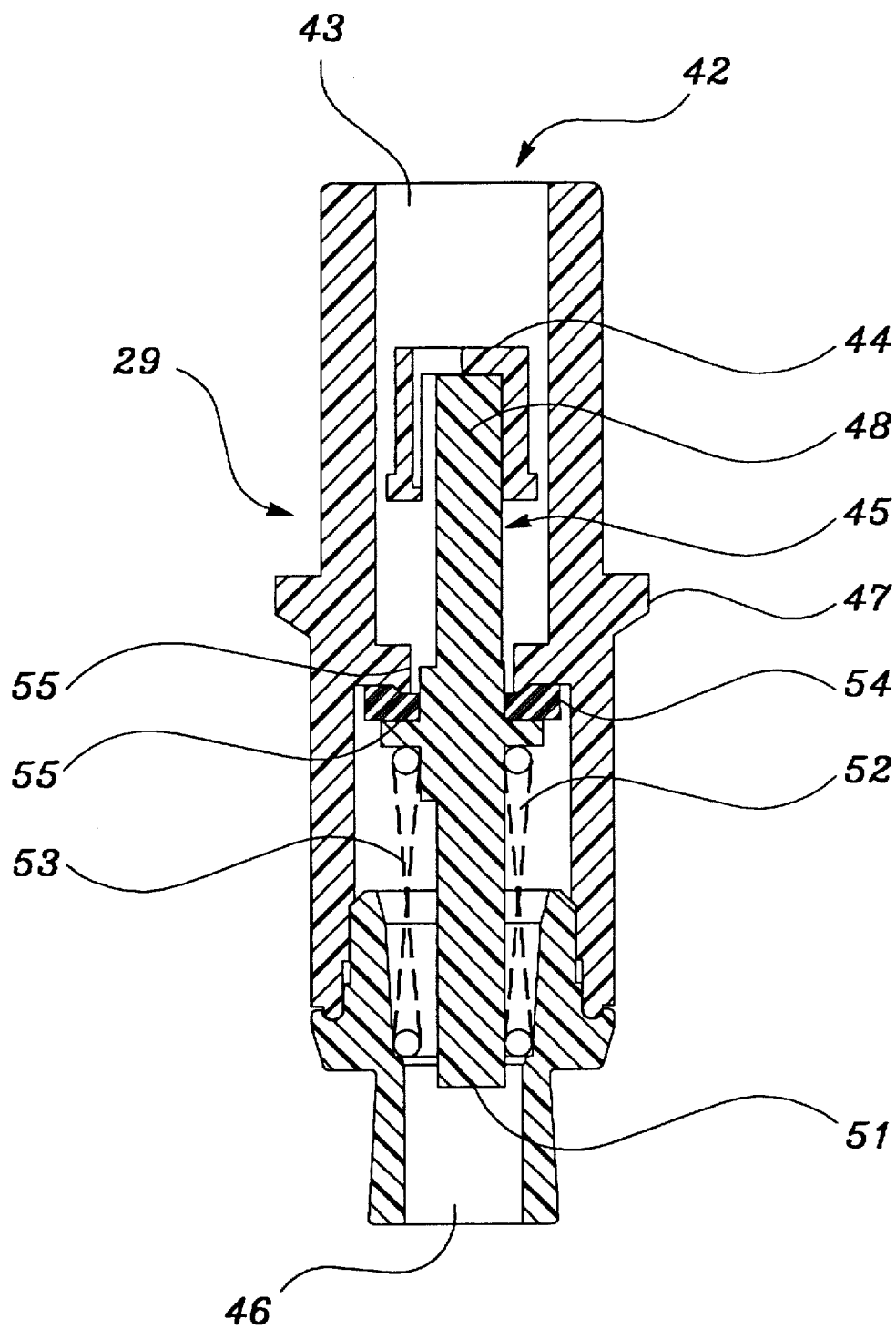
FIG. 9 is a cross-section of the access valve according to the present invention.

Referring now to FIG. 9, the basic operation of BESPAK valve 29 will be discussed. Valve 29 is a spring loaded valve that is normally closed to fluid flow communication. Distal opening 42 opens into a first interior chamber 43 where an activation piece 44 is disposed therein and attached to the distal end 48 of push rod 45. Rod 45 comprises distal end 48 that is disposed within first interior chamber 43, a middle portion 49 that includes an annular flange 50 and a proximal end 51 which are all disposed within a second interior chamber 52. The first interior chamber 43 and second interior chamber 52 are separated by aperture 61 which permits rod 45 to pass therethrough. Middle portion 49 includes a rubber seal 54 on a first side of portion 49 that seals the aperture 61 from fluid flow communication therethrough between first interior chamber 43 and second interior chamber 52. The distal end of spring means 53 is attached to a second side of middle portion 49 while the proximal end of spring means 53 is attached to the walls forming the proximal opening 46. Spring means 53 creates a continual forward bias towards distal opening 42, so that rubber seal 54 closes off fluid flow communication between first and second interior chambers 43 and 52 unless push rod 45 is properly activated.

Activation of push rod 45 is accomplished by the practitioner inserting the luer tip of a syringe (not shown) into the distal opening 42 of valve 29 until the luer tip contacts the activation piece 44. As the practitioner pushes downward onto the activation piece 44, the push rod 45 along with rubber seal 54 is moved towards the proximal opening 46, thereby opening aperture 61 and permitting fluid flow communication therethrough between the first interior chamber 43 and first interior chamber 52. Once middle portion 49 of rod 45 abuts interior flange 55, the forward motion of the luer tip is stopped and the syringe is fully engaged with valve 29 and ready for use.

Figure 10:
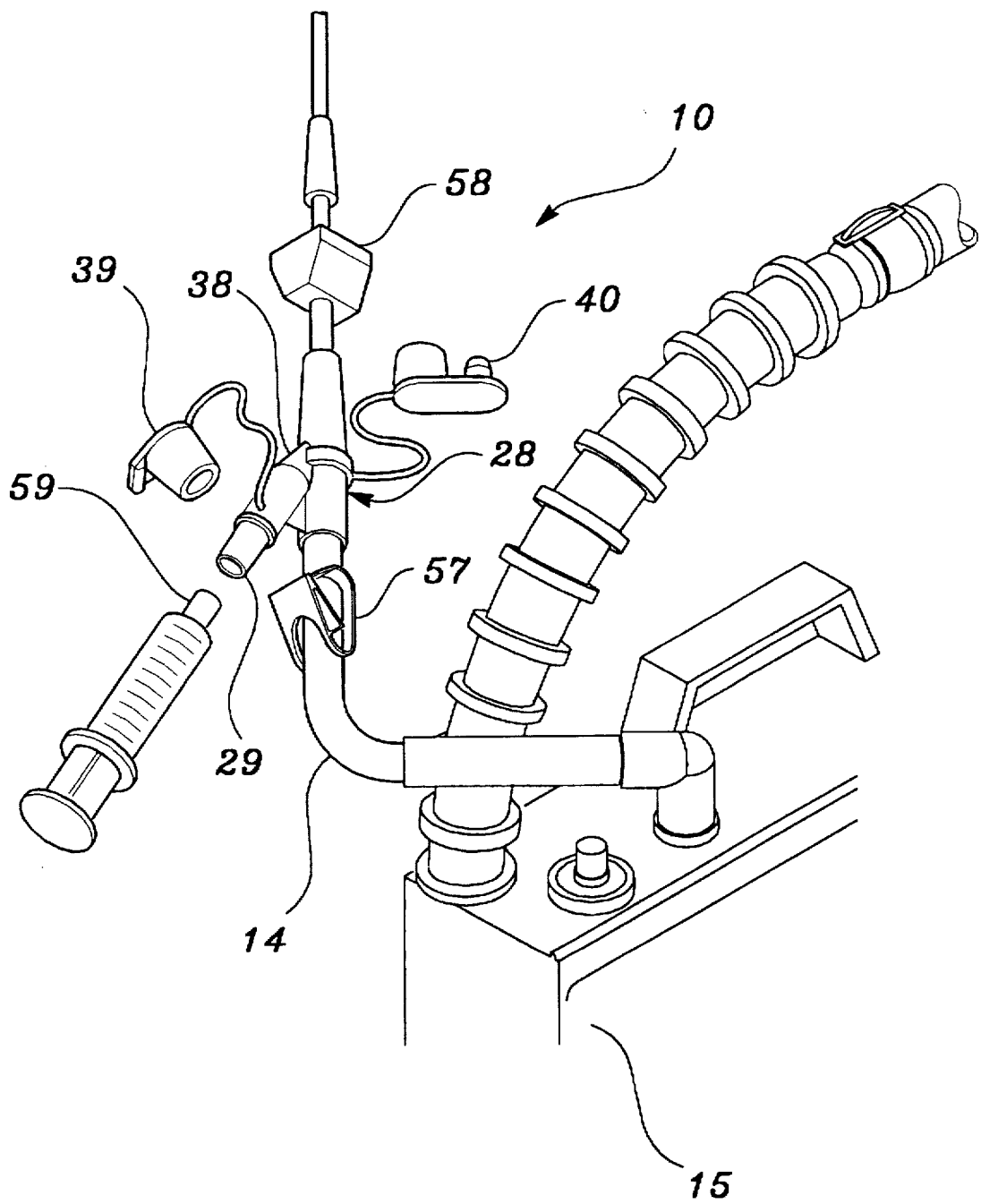
FIG. 10 is a perspective demonstrating the related method of using a standard luer tip syringe for accessing the autotransfusion system through the two-way valve in order to prime, sample, aspirate, flush and inject medication into the system.

Referring now to FIG. 10, the preferred method of using the syringe 56 to prime, sample, aspirate, flush or inject medication into the autotransfusion system 10 will now be discussed. The preferred method of priming system 10 in the absence of an infusion pump requires the practitioner to first clamp off infusion tubing 14 leading from the collection chamber 15 using the hose clamp 57 to cut off fluid flow communication therethrough. Once the clamp 57 shuts off fluid flow, the practitioner removes the first dust cap/plug combination 40 from the spike port 36 and attaches a conventional microaggregate filter 58 thereto. The practitioner then uncaps second dust cap/plug combination 39 from access port 38 and inserts the luer tip 59 of syringe 56 into valve 29 of port 38 until the tip 59 fully engages valve 29, so that fluid flow communication is established between valve 29 and the interior chamber 41 of Y-site connector 28. After the syringe is fully engaged, the practitioner inverts connector 28, as shown in FIG. 9, unclamps clamp 57, and pulls back on plunger 60 of syringe 56 until fluid begins to appear inside syringe 56, thereby indicating that sufficient vacuum has been achieved within system 10. The practitioner then disengages syringe 56 from valve 29 and reinserts second dust cap/plug combination 39 onto access port 38.

The preferred method of sampling system 10 requires the practitioner to uncap second dust cap/plug combination 39 from access port 38 and insert the luer tip 59 into valve 29 until fully engaged thereto. The practitioner then pulls back on plunger 60 until a sufficient amount of sample is taken into syringe 56. Upon completion of the sampling step, the luer tip 59 is withdrawn from valve 29 and the second dust cap/plunger combination 39 is reinserted over access port 38.

The preferred method of aspirating system 10 requires the practitioner to again uncap second dust cap/plug combination 39 from port 38 and insert the luer tip 59 into valve 29 until fully engaged thereto. With the plunger 60 in the full pull back position and the syringe filled with air, the practitioner pushes the plunger 60 forward until all the air is released into system 10. After the aspiration step is complete, the second dust cap/plug combination 39 is reinserted over access port 38.

The preferred method of flushing the system of clots and other debris requires the practitioner to first turn off the infusion pump (not shown). The practitioner then uncaps the second dust cap/plug combination 39 and inserts luer tip 59 into the valve 29 as disclosed above in the priming and sampling steps. With the plunger 60 in the full pull back position and the syringe 56 filled with saline, the practitioner pushes the plunger 60 forward until all of the saline is released into system 10. Once the flushing step is complete, the second dust cap/plug combination 39 is reinserted over the access port 38.

Finally, the preferred method of injecting medication into system 10 requires the practitioner to perform the same steps as in flushing with the exception that the infusion pump is not turned off and syringe 56 is filled with some type of medication to be injected into system 10 instead of saline solution.

Although the applicants have so far disclosed a novel combination and related method for priming, sampling, aspirating, flushing and injection medication into autotransfusion system 10 using valve 29 to gain access thereto through Y-site connector 28, the applicants also intend to use the valve 29 and Y-site connector 29 in combination with other fluid collection devices. For example, the Y-site connector 28 can be used in a urine collection device whereby the connector 28 and valve 29 are interposed between the patient and the collection bag at a point along the catheter that allows for ready access.

Although particular embodiments of the invention have been shown, it is not intended that the invention be limited thereby, instead, the scope of the present invention is intended to be limited only by the appended claims.

I claim:

1. In combination, a two-way valve and drainage unit for liquid priming, sampling, flushing and injecting fluid into a fluid collection system, comprising:

a valve connector having a distal opening, proximal opening, access opening, and an interior chamber, a first tube being attached to said distal opening and a second tube being attached to said proximal opening;

the two-way valve having a distal end and proximal end, said distal end forming a receptacle for receiving a liquid sampling, flushing and injecting device, said proximal end being disposed within said connector and in fluid flow communication with said interior chamber;

a pump attached to said second tube, said second tube being interposed between said pump and said connector;

a drainage unit having a fluid collection chamber, said drainage unit being attached to said first tube, said first tube being interposed between said drainage unit and said connector, whereby said first tube carries fluid from said drainage unit to said connector and said second tube carries fluid from said connector to said pump.

2. The combination according to claim 1, wherein said first tube carries fluid from said collection chamber of said drainage unit.

3. The combination according to claim 1, wherein the valve is insertable into said access opening.

4. The combination according to claim 1, wherein the pump is an infusion pump.

5. The combination according to claim 1, wherein the drainage unit is a chest drainage unit.

6. The combination according to claim 5, wherein the chest drainage unit is an autotransfusion chest drainage unit.

* * * * *